United States Patent
Lui et al.

(10) Patent No.: US 6,712,791 B2
(45) Date of Patent: Mar. 30, 2004

(54) SPLITTABLE MEDICAL VALVE

(75) Inventors: Chun Kee Lui, Monroeville, PA (US); William J. Boyle, Lower Burrell, PA (US)

(73) Assignee: Cook Vascular Incorporated, Leechburg, PA (US)

( * ) Notice: Subject to any disclaimer, the term of this patent is extended or adjusted under 35 U.S.C. 154(b) by 0 days.

(21) Appl. No.: 09/751,017

(22) Filed: Dec. 28, 2000

(65) Prior Publication Data

US 2001/0049499 A1 Dec. 6, 2001

Related U.S. Application Data

(60) Provisional application No. 60/173,758, filed on Dec. 30, 1999, and provisional application No. 60/232,519, filed on Sep. 14, 2000.

(51) Int. Cl.[7] .............................................. A61M 5/178
(52) U.S. Cl. ................................. 604/167.04; 604/160
(58) Field of Search ................................. 604/160, 161, 604/169, 167.04, 158, 264, 166.01, 905, 236, 202, 201, 200; 251/368, 149.1

(56) References Cited

U.S. PATENT DOCUMENTS

| | | |
|---|---|---|
| 4,345,606 A | 8/1982 | Littleford |
| 4,411,654 A | 10/1983 | Boarini et al. |
| 4,581,025 A | 4/1986 | Timmermans |
| 4,626,245 A | 12/1986 | Weinstein |
| 4,932,633 A | 6/1990 | Johnson et al. |
| 4,946,133 A | 8/1990 | Johnson et al. |
| 4,960,412 A | 10/1990 | Fink |
| 4,978,341 A | 12/1990 | Niederhauser |
| 5,000,745 A | 3/1991 | Guest et al. |
| 5,098,392 A | 3/1992 | Fleischhacker et al. |
| 5,098,393 A | 3/1992 | Amplatz et al. |
| 5,104,389 A | 4/1992 | Deem et al. |
| 5,125,903 A | 6/1992 | McLaughlin et al. |
| 5,125,904 A | 6/1992 | Lee |
| 5,167,634 A | 12/1992 | Corrigan, Jr. et al. |
| 5,167,637 A | 12/1992 | Okada et al. |
| 5,180,372 A | 1/1993 | Vegoe et al. |
| 5,207,656 A | 5/1993 | Kranys |
| 5,250,033 A | 10/1993 | Evans et al. |
| 5,273,546 A | 12/1993 | McLaughlin et al. |
| 5,312,355 A | 5/1994 | Lee |
| 5,350,363 A | 9/1994 | Goode et al. |
| 5,397,311 A | 3/1995 | Walker et al. |
| 5,409,463 A * | 4/1995 | Thomas et al. .............. 604/167 |
| 5,409,464 A | 4/1995 | Villalobos |
| 5,441,504 A | 8/1995 | Pohndorf et al. |
| 5,538,505 A | 7/1996 | Weinstein et al. |
| 5,549,576 A | 8/1996 | Patterson et al. |
| 5,562,632 A | 10/1996 | Davila et al. |
| 5,613,953 A | 3/1997 | Pohndorf |
| 5,613,956 A | 3/1997 | Patterson et al. |
| 5,720,759 A | 2/1998 | Green et al. |

(List continued on next page.)

FOREIGN PATENT DOCUMENTS

EP  0631793  1/1995

*Primary Examiner*—Manuel Mendez
(74) *Attorney, Agent, or Firm*—Brinks Hofer Gilson & Lione

(57) ABSTRACT

A splittable medical valve is disclosed that is configured with a interfacing region that permits the valve to be placed over or inside of a tubular medical device, such as a splittable introducer sheath, to prevent loss of bodily fluids and/or reduce ingress of air-borne pathogens. The valve further includes a sealing element configured to accept passage of a medical device, such as a catheter, sheath, pacemaker lead, or other ancillary device therethrough, whereby the valve body is split along one or more lines or fissure to allow removal of the valve from around the ancillary device.

30 Claims, 8 Drawing Sheets

U.S. PATENT DOCUMENTS

| | | |
|---|---|---|
| 5,755,693 A | 5/1998 | Walker et al. |
| 5,755,775 A | 5/1998 | Trerotola et al. |
| 5,800,384 A | 9/1998 | Russell et al. |
| 5,827,228 A | 10/1998 | Rowe |
| 5,843,031 A | 12/1998 | Hermann et al. |
| 5,865,807 A | 2/1999 | Blake, III |
| 5,895,377 A | 4/1999 | Smith et al. |
| 5,935,112 A | 8/1999 | Stevens et al. |
| 6,083,207 A | 7/2000 | Heck |
| 6,090,067 A | 7/2000 | Carter |

* cited by examiner

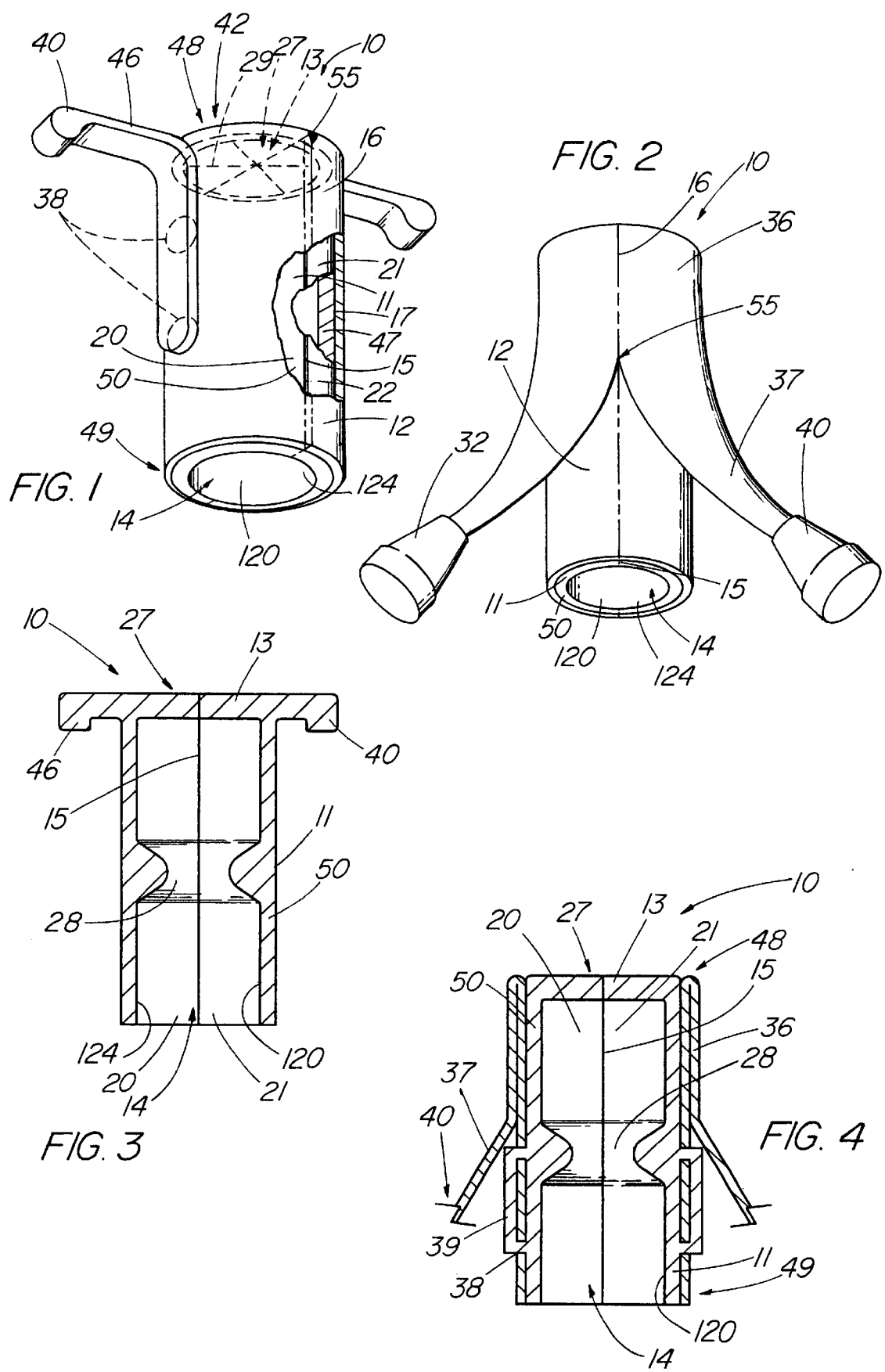

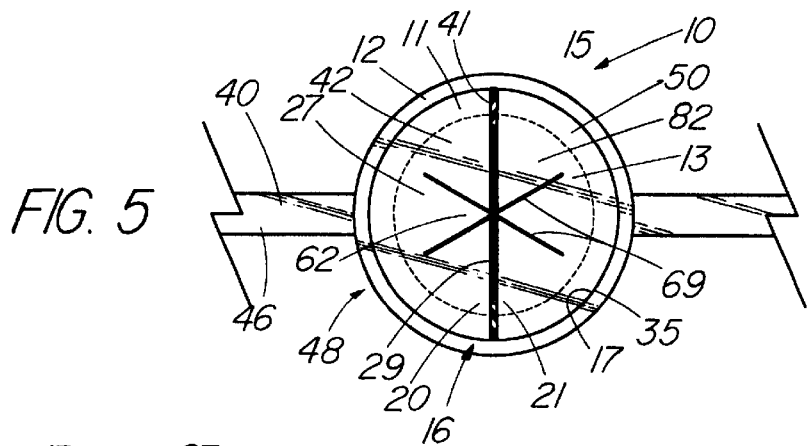
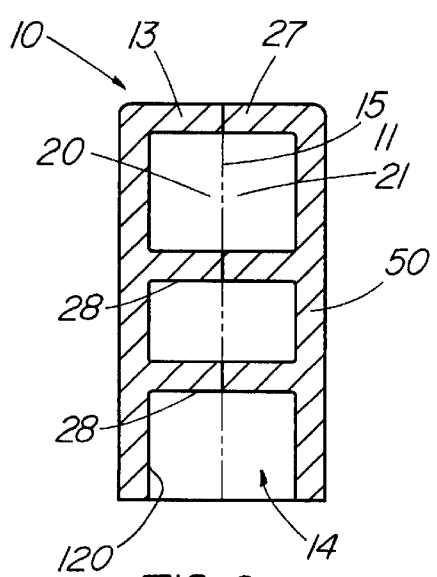
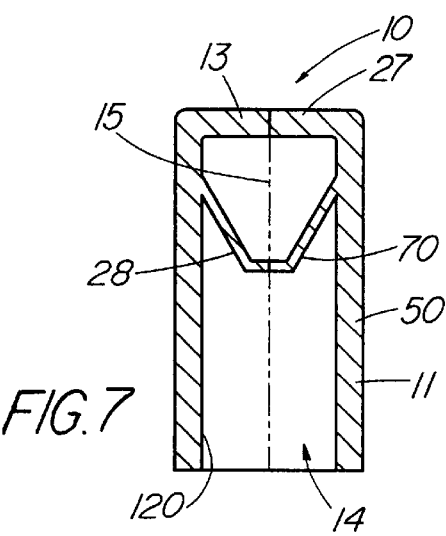
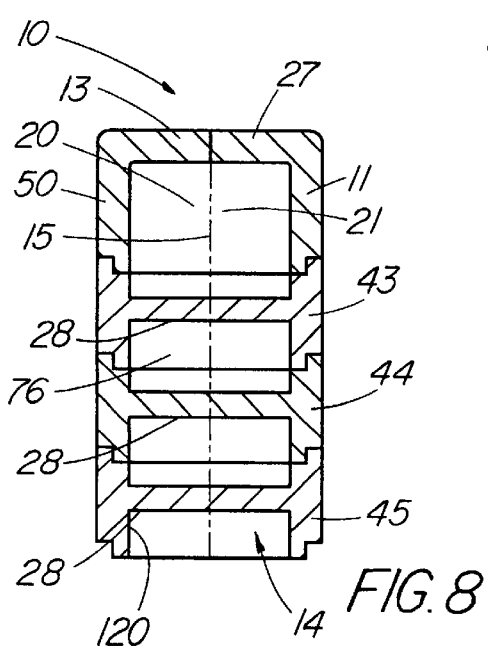
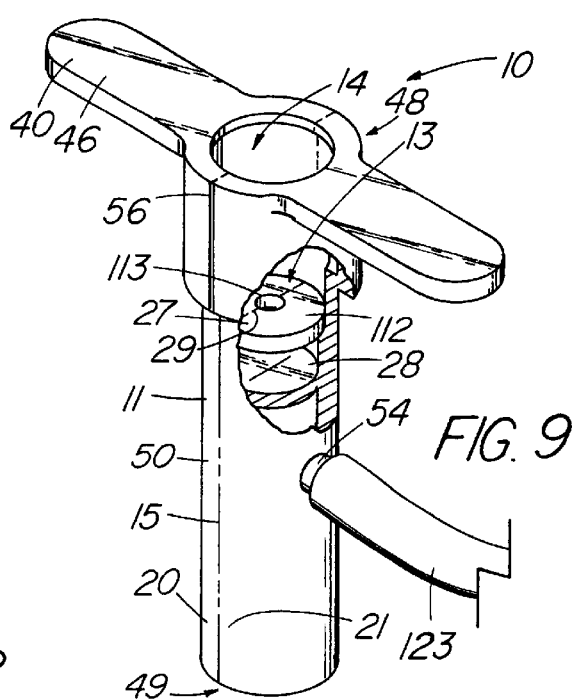

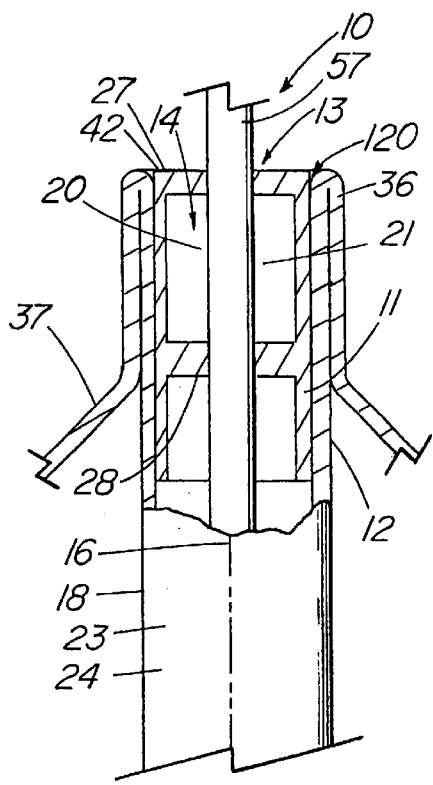
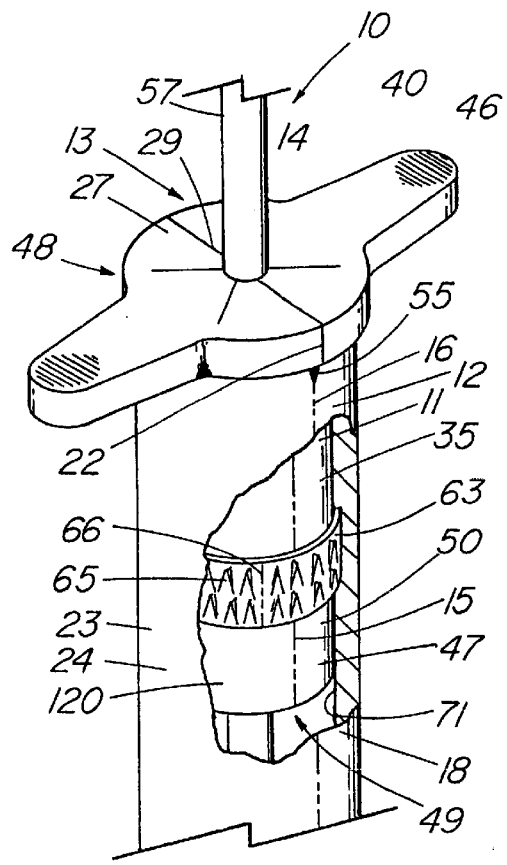
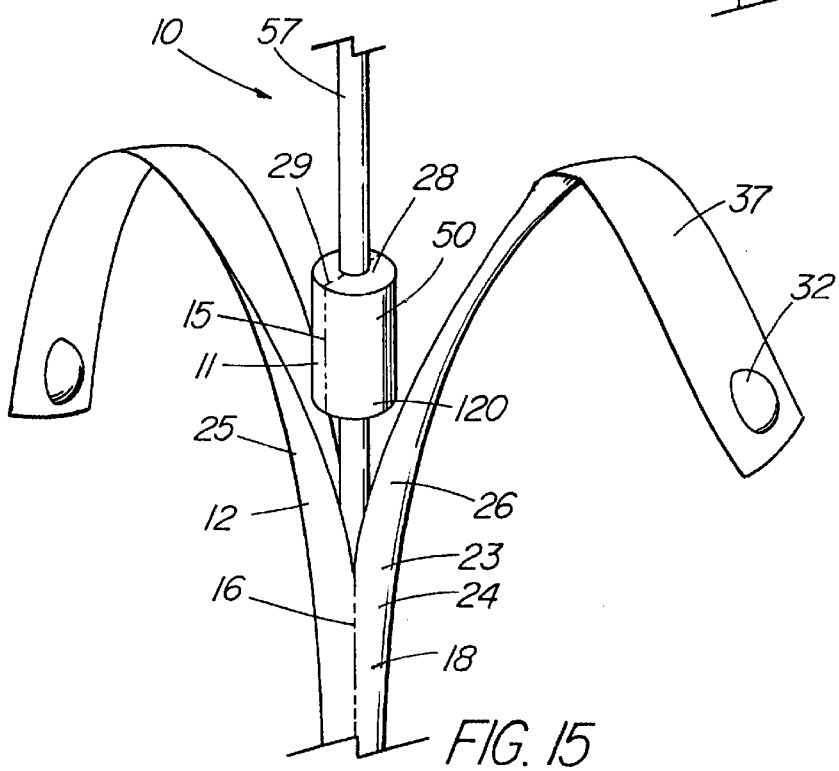

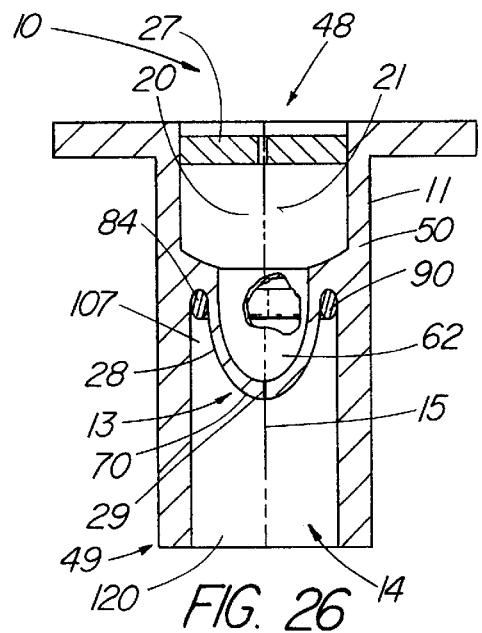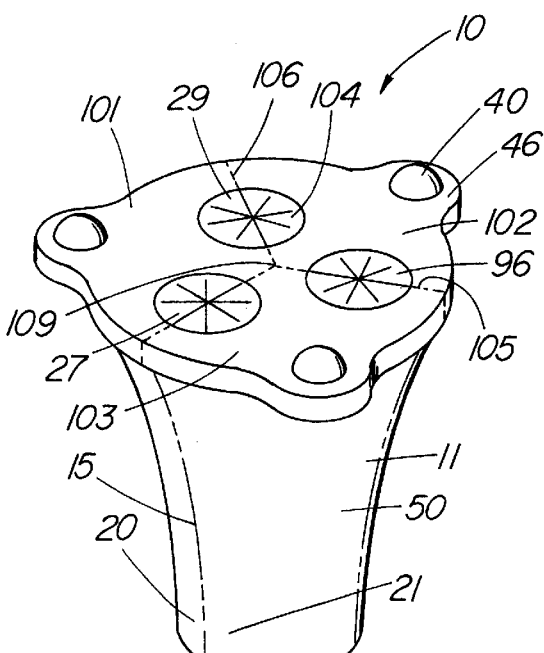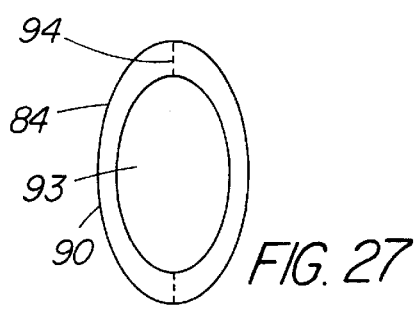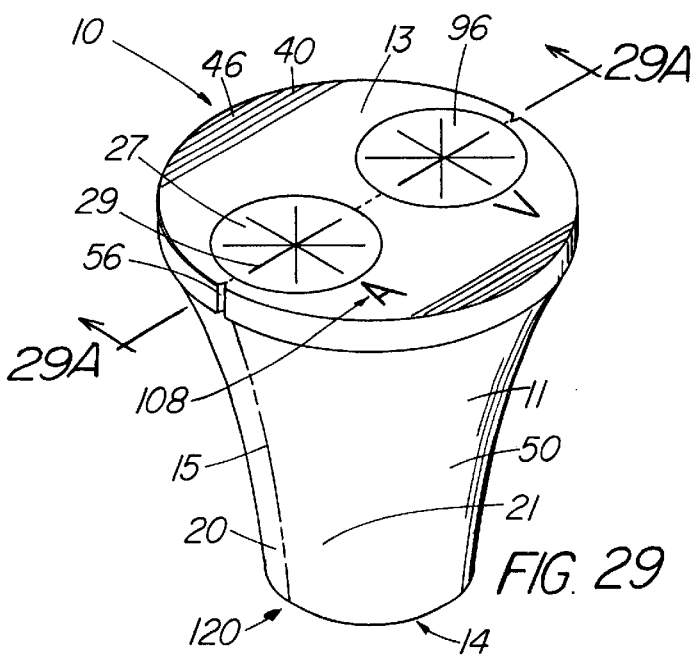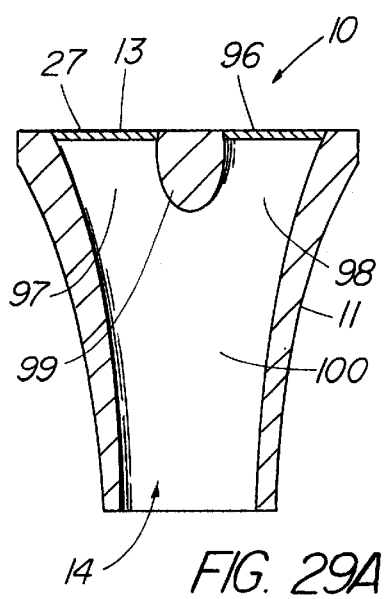

SPLITTABLE MEDICAL VALVE

CROSS-REFERENCE TO RELATED APPLICATIONS

This application claims priority of provisional application Ser. No. 60/173,758, filed Dec. 30, 1999 and Ser. No. 60/232,519, filed Sep. 14, 2000.

TECHNICAL FIELD

This invention relates to medical devices, in particular to hemostatic valves for intravascular devices.

BACKGROUND OF THE INVENTION

Percutaneous placement of intravascular catheters, pacemaker leads, etc. involves blood loss, that while easily controllable, especially during venous access, can become significant during long procedures. For example, procedures such as placement of leads in the coronary sinus for biventricular pacing, can last 4 hours, during which time the blood loss of up to 500–600 cc can represent a risk to the patient. Additionally, the open conduit into the body can become a source of infection to the patient. To help reduce these potential risks, self-sealing hemostatic valves have been developed for use with introducer sheaths. These valves provide a seal against flashback of blood from the proximal end of the sheath, including when a second device is being manipulated within the introducer.

Medical devices with large proximal fittings, such as pacemaker leads and PICC lines, cannot be readily used through standard hemostasis valves and introducers because of the need to remove the introducer while leaving the other device in place. To address this need, splittable sheaths and hemostasis valves were developed so that the introducer and valve can be removed while the inner device remains in the patient. Combinational devices exist, such as the SAFE-SHEATH™ Splittable Valved Sheath System (Pressure Products, Inc., Rancho Palos Verdes, Calif.), which is comprised of a splittable valve attached to the end of a scored introducer sheath. The valve housing containing the valve membrane is split along scores lines which are aligned with score lines that continue down the length of the integral introducer. Thus, the valve and introducer are split together. One disadvantage of this combinational system is the lack of flexibility in how the device is used. For example, to place a coronary sinus pacemaker lead, a physician will often wish to advance the long introducer sheath into the coronary vessel, then partially withdraw the sheath, perhaps 10 cm, prior to introducing the pacing lead. The large integral valve at the proximal end of the sheath cannot enter the patient; therefore, the physician must have an undesirably long section of introducer exiting the patient, where ideally, he or she would like to peel the introducer back closer to the entry site. In addition, the scored introducer portion of the SAFE-SHEATH™ lacks the structural integrity to negotiate tortuous bends of the coronary vessels. Because the valve and introducer are designed only to be used together, the system cannot be adapted to work with different sheaths and other intravascular devices that may offer important clinical advantages in certain procedures.

What is needed is a simple system that offers greater flexibility to fully manipulate and adjust the splittable sheath prior to splitting away the valve. It would also be desirable to have a splittable valve that can be used with different splittable sheaths that did not require integral attachment or alignment of split lines. Further considerations include having a splittable hemostatic valve of simple construction that is easy to use, inexpensive to manufacture, and can provide superior sealing characteristics, even in the presence of high backflow pressures such as are seen in arterial applications.

SUMMARY OF THE INVENTION

The foregoing problems are solved and a technical advance is achieved in a splittable hemostatic valve that includes an interfacing region sized and configured to permit the valve to be coupled to a separate splittable introducer sheath or other tubular medical device to permit passage of a catheter or device therethrough with minimal blood flashback. In a first embodiment, the hemostatic valve can be placed over a splittable introducer sheath, such as a PEEL-AWAY® Introducer Sheath (COOK Incorporated, Bloomington, Ind.) while typically, a dilator is initially co-introduced, followed by the device being placed, such as a pacemaker lead or intravenous catheter having a large proximal hub or fitting. The hemostatic valve can then be split and removed from the introducer, which is also split apart, leaving the indwelling device undisturbed. Advantageously, the replaceable aspect of the valve allows the physician the ability to partially withdraw the introducer and peel it back down, as is often done when placing certain intravascular devices, and then place the hemostatic valve back over the new proximal end that is formed. This provides a significant clinical benefit over existing splittable introducers that include an integral valve at the proximal end that is split along with introducer, thereby not allowing for replacement at a more distal location. In another embodiment, the interfacing region can be configured to be placed at least partially within the passageway of the introducer sheath, instead of over the sheath's outer surface.

The hemostatic valve comprises a valve body which is typically made of silicone or another elastic material that allows the valve to be fitted over or into the introducer sheath while offering some sealing characteristics. The hemostatic valve includes one or more sealing elements located within the valve passageway. In some embodiments of the invention, one or more of the sealing elements are formed to be integral with the valve body. They can be positioned at the proximal end or within the body of the valve and may include slits or apertures to allow passage of a medical device. Other embodiments include a valve insert disk made of silicone foam that is separately formed and affixed within the hemostatic valve passageway.

In various other aspects of the present invention, the proximal end of the hemostatic valve may be configured to receive and lock a dilator hub such that the dilator and introducer can be maintained in the proper longitudinal alignment with each other during the procedure. In addition, the distal end of the valve can be configured to accept a series of specific-sized introducers by including a multiple steps of different diameters (e.g., 3.5 to 6.0 Fr). In another aspect, the valve can include a side port to allow access to the passageway for procedures such as an I.V. drip, system flushing, air evacuation, or the infusing of medicaments or contrast media.

The hemostatic valve includes at least one line of fissure through which the valve is opened to allow external access to the passageway. In one embodiment, the silicone valve body is formed with opposing scores or grooves formed nearly all the way through the inside or outside of the valve wall such that the two valve halves can be readily pulled apart when the two integral tabs are pulled outward to initiate the split. Typically, the sealing elements are correspondingly scored or split to facilitate a complete separation of the valve assembly.

In another aspect of the invention, the valve is constrained by a splittable outer sheath, such as one made of molecularly oriented, anisotropic PTFE used to make the PEEL-AWAY® Introducer Sheath. The embodiment also includes a means to grasp and tear the sheath away to open the valve, which may be restrained as two separated halves that fall apart, or scored or so affixed as to be torn apart by the separating action of the sheath.

In another aspect of the invention, the distal portion of the hemostatic valve assembly includes a splittable distal extension of the valve body that is adapted to fit over or couple with a particular medical device. Many intravascular introducers and other devices, unlike the Cook PEEL-AWAY® Introducer, have a large proximal fitting. In one embodiment, a distal portion is adapted to accept and seal about the proximal fitting of a standard introducer sheath. The distal portion could include a series of seals that are designed to fit over a multiplicity of fittings, making it a 'universal' splittable hemostatic valve.

In yet another aspect of the invention, a sealant filler material is provided within the passageway of the hemostatic valve, preferably within one or more cavities formed between the self-sealing membranes. While the self-sealing membranes provide an adequate barrier against fluid backflow when used in the venous system where pressures typically average around 0.2 psi, arterial pressures represent over a ten fold increase over that of the venous side, making sealing much more difficult. This sealant filler material, which provides an additional blood barrier, can comprise virtually any biocompatible material that can provide a seal around a device being passed through the valve. Possible materials include a viscous liquid such as glycerine; a gel; a foam or sponge; densely-packed solid particles such as minute beads or fibrous material; and strips of material such as collagen. These materials can be affixed to or incorporated into the valve body or introduced into the existing cavity, such as via a side port or injected through the valve body wall. Membranes can be used to longitudinally divide the cavity into two halves that are filled with a substance that allows the subcavities to be resiliently depressed. The resulting counter force against the residing device provides a seal with the membranes allowing the contents of the subcavities to remain contained when the valve is separated.

In still yet another aspect of the invention, a biasing means is included to provide additional force against the leaflets of the distal seal, such as a duck-bill valve, to provide improved sealing properties. In one embodiment, the biasing means comprising two biasing elements of a material such as silicone which are added to the valve after fabrication. The biasing elements are added by applying force to the valve on opposite sides such that the force is in line with a valve slit, thereby causing it to open slightly. The silicone or other material is then added adjacent to the valve leaflets at points perpendicular to the valve slit and allowed to cure. The force is released, returning the valve to its original shape with the cured biasing elements now functioning to continuously urge the leaflets closed. In other embodiments, the biasing means comprises an O-ring or sleeve that is included within the valve after the valve with slit is formed to provide a biasing force to urge the leaflets into the closed position.

In still yet another aspect of the invention, the valve assembly can include a plurality of valves whose passageways are joined distally into a common passageway. In an embodiment having two proximal seals with two passageways each representing bifurcations of the single common passageway, there are two oppositely placed lines of fissure that allow the valve assembly to be separated into two halves. In an embodiment having three proximal seals and three passageways that feed into a single common passageway, there are three lines of fissure that allow the valve assembly to be separated into three pieces to allow introduced devices to remain in place. Additional valves and entry passageways are also contemplated.

BRIEF DESCRIPTION OF THE DRAWINGS

FIG. 1 depicts a partially-sectioned pictorial view of an embodiment of the splittable hemostatic valve assembly having a outer sheath;

FIG. 2 depicts a pictorial view of an alternative embodiment of the present invention having an outer sheath;

FIG. 3 depicts a cross-sectional side view of an embodiment of the present invention having a plurality of sealing elements;

FIG. 4 depicts a cross-sectional side view of the hemostatic valve assembly of FIG. 2;

FIG. 5 depicts a top view of the embodiment of FIG. 1;

FIGS. 6–8 depicts cross-sectional views of various sealing element embodiments of the present invention;

FIG. 9 depicts a pictorial view of an embodiment of the present invention having a side port;

FIG. 14 depicts a partially-sectioned side view of an embodiment of the present invention adapted to be placed within an introducer sheath;

FIG. 15 depicts a pictorial views of a second embodiment that is adapted for placement within a introducer sheath;

FIG. 16 depicts a partially-sectioned pictorial view of an embodiment of the present invention adapted to be partially placed within an introducer sheath;

FIG. 26 depicts a cross-sectional view of a hemostatic valve having a second embodiment of a biasing means;

FIG. 27 depicts a top view of the biasing means of FIG. 26;

FIG. 29 depicts a pictorial view of an embodiment of a splittable valve assembly having two proximal valves with a common central passageway;

FIG. 29A depicts a cross-sectional view taken along line 29A—29A of the embodiment of FIG. 29;

FIG. 30 depicts a pictorial view of an embodiments of a splittable valve assembly having three proximal valves with a common central passageway;

DETAILED DESCRIPTION

Figure 10:
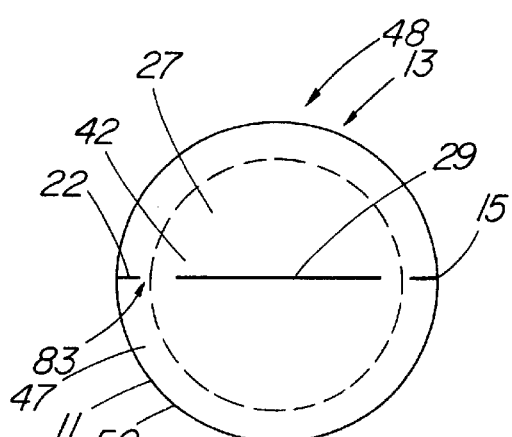
FIG. 10 depicts a top view of an embodiment of a valve body of the present invention having a external score line.

A better understanding of the present invention will now be had upon reference to the following detailed description, when read in conjunction with the accompanying drawing, wherein like reference characters refer to like parts throughout the several views and different embodiments of the present invention.

Figure 11:
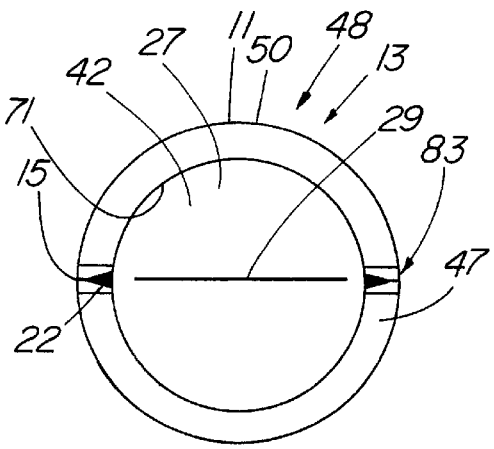
FIG. 11 depicts a bottom view of an alternative embodiment of a valve body of the present invention having an internal score line.
Figure 12:
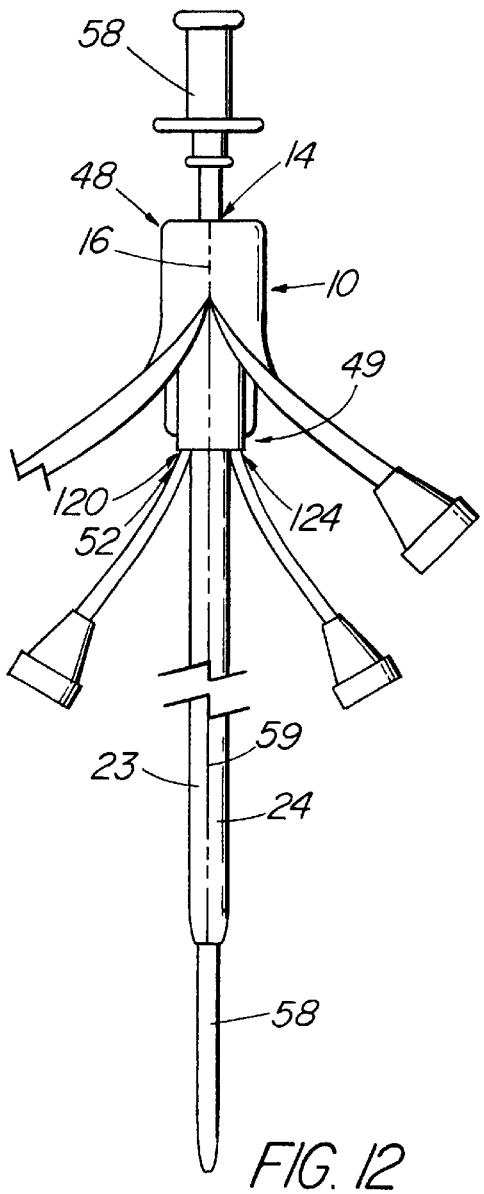
FIG. 12 depicts a side view of the embodiment of FIG. 1 being used with a splittable introducer sheath.
Figure 32:
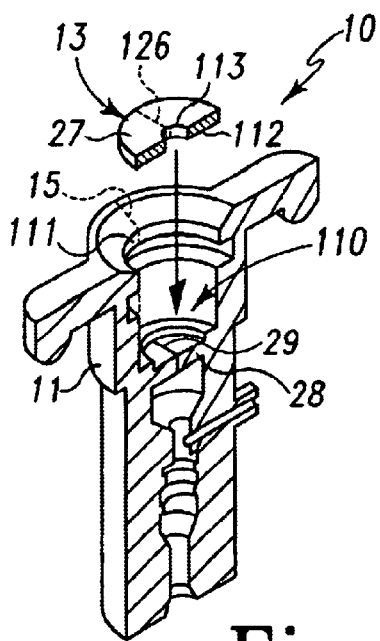
FIG. 32 depicts an exploded pictorial view of the embodiment of FIG. 9.
Figure 33:
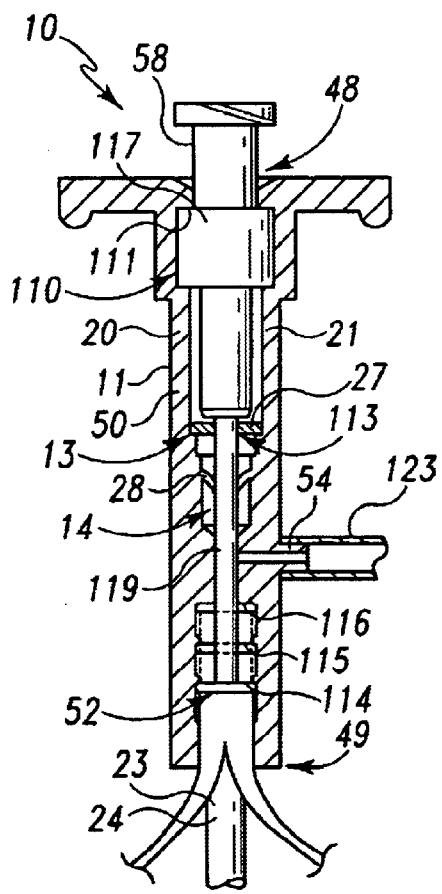
FIG. 33 depicts a partially sectioned view of an embodiment similar to that of FIG. 9 being used with a dilator and introducer sheath.

The splittable valve assembly 10 of the present invention, as embodied in FIGS. 1–34, comprises a hemostatic valve 11 that includes a valve body 50 with a passageway 14, at least one line of fissure 15 to permit the valve to split and allow external access along the length of the passageway, and at least one sealing element 13 configured to traverse the passageway 14, while permit the passage of an first medical device 57, such as a catheter, dilator, pacemaker lead, etc., while substantially preventing or eliminating the leakage or 'flashback' of blood or other bodily fluids. The splittable valve assembly 10 is designed for use with a second medical device, typically a tubular medical conduit 23 such as a splittable introducer sheath 24. The hemostatic valve 11 of the present invention comprises an interfacing region 120, typically located at the distal end 49 of the valve assembly. The interfacing region 120 is configured to permit the valve to be coupled or attached to the tubular medical conduit 23 at some point prior to or during the procedure involving the tubular medical conduit and in some instances, reattached, particularly when the valve is removed intact and the splittable introducer sheath is partially peeled down to form a new proximal end. In the illustrative embodiments such as FIGS. 1, 2, and 9, as well as others discussed later, the interfacing region 120 permits the splittable valve assembly 10 to be placed over the proximal end 52 of a splittable introducer sheath 24, as depicted in FIGS. 12, 19 and 33. If during the course of the procedure, the physician decides to partially withdraw and peel back down the sheath 24, the valve can be advantageously removed, rather than being split with the sheath 24, thereby allowing it to be placed intact back over the new proximal end of the splittable introducer sheath 24 and resume its function as a hemostatic valve 11 until such time as the first medical device 57 is introduced to its target location and the splittable introducer sheath 23 and hemostatic valve 11 are split apart and discarded. It should be noted that while valve portion 11 is referred to herein as a 'hemostatic valve,' it has possible applications in other types of non-vascular procedures where there is a desire to prevent leakage of fluids and/or reduce exposure to air-borne pathogenic organisms. For example, the splittable valve assembly 10 of the present invention can be used in minimally invasive neurological procedures to limit contact of the cerebral spinal fluid with ambient air. Another possible application would be urological procedures where the valve could help prevent the introduction of pathogenic organisms into the urinary tract.

A basic embodiment of the present splittable valve assembly 10 is depicted in FIGS. 9 and 31–33. In this embodiment, the valve body 50 is insert molded into a single piece or unit from medical grade silicone, although other elastomeric polymers can be used, including combinations of different compounds for different portions of the valve. To facilitate splitting of the valve body 50 into separate first and second halves 20,21 to expose the passageway 13 of the hemostatic valve 11, opposing lines of fissure 15, located about 180° with respect to each other, are formed in the wall 47 of the valve body. The lines of fissure 15 of the illustrative embodiment each comprise a score line 22 or groove formed partially through the wall 47, leaving a small amount of material 83 (e.g., 0.01") as a bridge to join the adjacent halves 20,21. The hemostatic valve 11 can be molded as a single unit and scored to create a line of fissure 15 to facilitate rupture of the valve body 50 when the respective halves 20,21 are pulled outward in opposite directions. In the embodiments of FIGS. 9–10, the score line 22 is formed into the outside surface 35 of the valve wall 47. To facilitate separation of the valve body 50 along the score line 22, a starter split 56 or notch can be made at the distal end of the hemostatic valve 11 at the line of fissure 15. The valve body 50 is separated by using the integral tabs 40, thus permitting the initial separation force to be concentrated at the distal end 49 where the starter split 56 is located. FIG. 11 depicts yet another embodiment in which the score line 22 in formed into the inside surface 71 of the wall. If the hemostatic valve 11 is insert molded into the outer sheath 12, scoring could occur by either running the scoring tool along the passageway 14 of the hemostatic valve 11, or configuring the die to create a score line 22 in the valve body 50 during the molding process such that the two valve halves 20,21 were bridged by a thin membrane 83 of material. A line of fissure 15 can be formed using a number of well-known techniques and assume a variety of configurations to achieve the goal of providing a relatively predictable path through which the split in the valve body progresses, such that the hemostatic valve can be removed from around the first medical device 57.

Returning to the embodiment of FIGS. 9 and 31–33, at the proximal end 48 of the hemostatic valve 11 are located two grasping elements 40 which in this embodiment, comprise integral tabs 46 that integrally extend from valve body 50 of the hemostatic valve 11. These grasping elements 40, which facilitate splitting the valve, can assume a wide variety of configurations, both integral, and separate from the valve body 50 with selected examples being depicted in various other figures. When the operator pulls the integral tabs 46 in opposite directions away from the valve body 50, the lines of fissure 15 split from the proximal end 48 progressing to the distal end 49, causing the valve body 50 to separate into halves 20,21. To initiate the split along the lines of fissure 15, an optional starter split 56 is included at the proximal end 48 whereby the lines of fissure 15 completely traverse the wall 47 for a relatively short distance (e.g., 2–7 mm) relative to the length of the hemostatic valve, which in the illustrative embodiment used with 3–12 Fr intravascular introducer sheaths, measures about 30–50 mm, depending on the size of the companion sheath.

Figure 19:
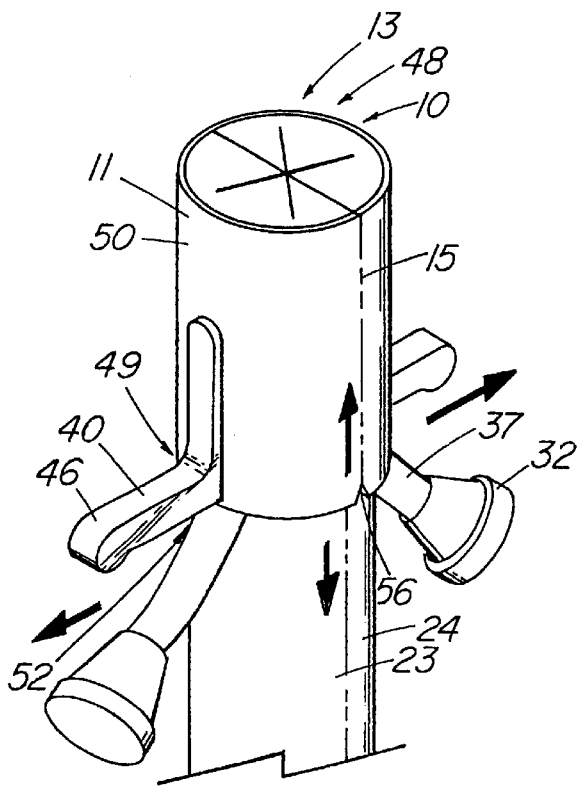
FIGS. 19–20 depict a pictorial views of embodiments of the present invention having a grasping member or members located at the distal end of the valve body.
Figure 20:
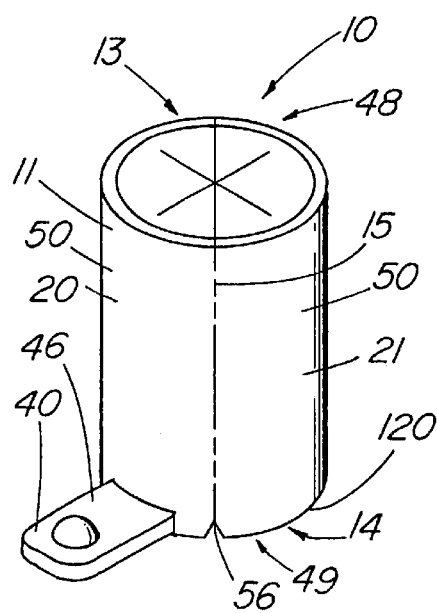

FIGS. 19–20 depict embodiments in which the hemostatic valve 11 is split starting from the distal end 49, proceeding to the proximal end 48. To better accomplish this, the grasping members 40 are located at the distal end 49 of the hemostatic valve assembly 10 for opening the line of fissure 15 toward the proximal direction, resulting in separation of the valve halves 20,21. FIG. 19 depicts an embodiment that is similar to that of FIG. 9 with the exception of the reversal of the grasping member 40 and starter split 56 orientation. As shown, the grasping members 40 are advantageously located in proximity to the splittable introducer sheath handles 32. If each pair of grasping members/handles are pinched together and pulled outward from the hemostatic valve assembly 10 and splittable introducer sheath 24, both devices can be split together. In doing so, the hemostatic valve 11 split initially continues upward from the starter split 56, while the splittable introducer sheath split initially progresses upward to the proximal end 52, then continues downward along a distal path. The line of fissure 15 may not extend the entire length of the valve body 50 if the starter split 56 or starter split plus a partial score line are sufficient, given the wall thickness and material, to force a split that continues all the way to the opposite end 48. FIG. 20 depicts a related embodiment that includes a single grasping member 40 and integral tab 46 that is located at the distal end 49 of the valve body 50 on only one half 20 of the valve. If the device over which the hemostatic valve 11 is placed extends a sufficient distance into the passageway 14 to provide adequate counter force against the opposite half 21, a single grasping element 40 located on the first half 20 can be used to cause a split that allows full separation of the valve body 50.

Figure 31:
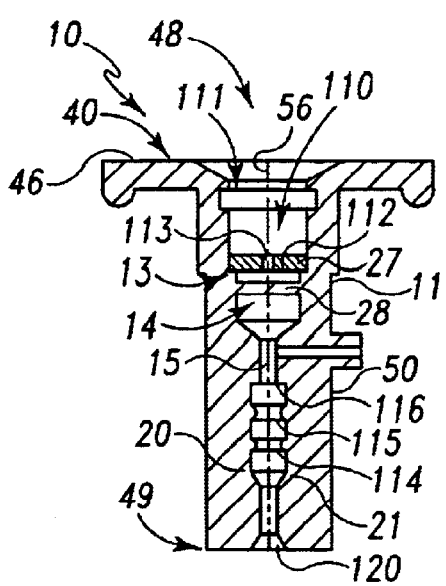
FIG. 31 depicts a sectioned view of the embodiment of FIG. 9.

The number and configuration of sealing element 13 of the present invention represents a design choice influenced by the type of procedure involved and the instrumentation to be used with the valve. In the embodiments of FIGS. 31–33, the illustrative hemostatic valve 11 includes two sealing elements 13 which comprise a proximal seal 27 and a distal seal 28. The distal seal 28 comprises a thin, 0.010" membrane that is integrally formed with the valve 50. A slit 29 is formed through the membrane to permit through passage of the first medical device 57, such as a dilator shaft 119, being introduced through the tubular medical conduit 23 for placement at the target site. In the illustrative embodiment, the proximal seal 27 comprises disk-shaped seal insert 112 made of silicone foam that is separately formed from the valve body 50, inserted into the passageway 14 and affixed with silicone adhesive or otherwise secured in placed. The seal insert 112 includes a small aperture 113 that facilitates smooth passage of a relatively large-diameter medical device therethrough. A transverse fissure 126 is made partially through the seal insert 112 in line with the lines of fissure 15 in the valve body to allow the seal to split in half along with the remainder of the hemostatic valve 11.

FIGS. 9 and 31–33 depict two related embodiments in which the proximal seal 27 is situated within the passageway 14 such that sufficient space exists between the proximal seal 27 and the proximal end 48 of the valve to form a proximal receiving chamber 110 that is configured to accept a dilator hub 117. A locking lip 111 that is located at the proximal end of the proximal receiving chamber 110 helps hold the dilator hub 117 therein. This permits the dilator 58 and introducer sheath 24 to advantageously remain in a constant positional relationship in which the distal tapers of the two devices 58,24 match while being manipulated within the patient. Because the valve body 50 is typically made of a flexible silastic material the dilator hub 117 can easily be pulled back out of the proximal receiving chamber 110 once the dilator 58 is ready to be removed from the introducer sheath 24. In the embodiments of FIGS. 31 and 33, the configuration of the proximal receiving chamber 110 varies depending on the size of the dilator and the design of its hub. The valve embodiment of FIG. 31 is designed for a smaller dilator hub (e.g., 4.5–7 Fr), while the embodiment of FIG. 33, accepts a larger, longer hub used with a larger dilator, such as that intended for use with a 10–12 Fr introducer sheath 24.

In valve embodiments that do not include a proximal receiving chamber 110, the proximal seal 27 is typically located at the proximal end 48 of the valve assembly 10 as depicted in a number of embodiments, including those in FIGS. 1–8. In one embodiment depicted in FIG. 5, the proximal seal 27 functions a self-sealing membrane 42 by virtue of one or more slits 29. In the embodiment, of FIG. 5 there is a first slit 29 comprising a portion of the line of fissure 15 that extends across the self-sealing membrane. Also included are two diagonal slits 69 that along with the first slit 27, define a series of opposing valve leaflets 62 that seal around a medical device placed through the passageway 14 of the hemostatic valve 11. To ease passage of a device through the self-sealing membrane 42, especially a small-diameter device such as a biventricular pacing lead, the valve leaflets 62 can be coated with a lubricious material such as SLIP-COAT™ or GRAFT-COAT™ (Sterilization Technical Services, Rush, N.Y.). With regard to the illustrative embodiment, the valve body 50 is contiguous with the sealing element 13, as both are formed of the same elastomeric material.

FIGS. 3 and 6–8 depict additional sealing element 13 embodiments. In each of the illustrative examples, there is a proximal seal 27 comprising a self-sealing membrane 42 with at least one slit 29, and at least one distal seal 28 to provide an additional barrier against flashback of blood or other bodily fluid. In the embodiment of FIG. 3, the distal seal 28 comprises an integral ring or constriction that provides an second sealing element 13 in addition to the self-sealing membrane 42 that comprises the proximal seal 27. In the embodiment of FIG. 6, there are a pair of distal seals 28, each comprising a disk-shaped self-sealing membrane 42 across the passageway 14 of the hemostatic valve 11. In the embodiment depicted in FIG. 7, the distal seal 28 comprises a duck-bill valve 70 with a central slit 29 wherein fluid flowing back toward the proximal end 48 of the valve helps force two halve of the valve 70 together and thus, assists with sealing about an device positioned in the passageway 14. It the embodiment of FIG. 8, the hemostatic valve 11 and proximal seal 27 are attachable to a series of additional seal components 43,44,45 that interlock into a single unit. Each component comprises a distal seal 28 and seal supporting structure 51 which collectively, form the valve body 50 of the expanded splittable valve assembly 10. It is anticipated that number of components can be varied to achieve the desired amount of protection against flashback of blood or bodily fluid within the passageway 14 of the hemostatic valve 11.

FIGS. 31–34 are exemplary of two basic types of interfacing regions 120 for coupling or attaching the hemostatic valve 11 to a tubular medical conduit 23. In the type depicted in FIGS. 31–33, which also the type found the embodiments depicted in FIGS. 1–13 and 19–30, the interfacing region 120 is sized and configured such that its contact surface 124 with the tubular medical conduit 23 is located within the passageway 14 of the hemostatic valve 11. Coupling occurs with the hemostatic valve 11 being placed over the proximal end 52 of the tubular medical conduit 23, as depicted in FIGS. 33, with other embodiments shown in FIGS. 12 and 19. Ideally, the passageway 14 at the distal end 49 of the hemostatic valve 11 is sized such that the proximal end 52 seals against the contact surface 124 to greatly reduce the possibility of leakage. Although it is within the scope of the invention for the valve body 50 to comprise a rigid or semi-rigid plastic or another non-elastic material, silicone or similar type materials provide superior sealing characteristics, as well as making it easier to split the valve body 50 along the lines of fissure 15.

In the embodiments of FIGS. 31–33, the interfacing region 120 is configured to accept different-sized introducer sheaths 24 by including a series of steps 114,115,116, each corresponding to a specific sized introducer. For example, in the embodiment of FIGS. 31–32, the first step 114, located closest to the distal end 49, a diameter to readily accommodate up to a 6.0 Fr introducer sheath 24 before the proximal end 52 of sheath abuts the proximal lip of the stop 114 and cannot be advanced further into the passageway 14. The second step 115, located proximal the first step 114, can accept up to a 4.5–5.0 Fr introducer sheath, while a 3.5–4.0 Fr introducer sheath can pass through the first two steps 114,115 before abutting the third step 116. Depending on the durometer of the valve body 50 material, it is possible for the valve body 50 to yield somewhat and accommodate a larger-size introducer sheath 24 that for which the particular stop is configured. The embodiment of FIG. 33 depicts an interfacing region 120 sized to accept either a 10, 11, or 12 Fr introducer sheath 24, the proximal end 52 of the latter of the three being shown positioned at the first step 114. The examples of FIGS. 31–33 are merely illustrative as to the number and range of steps. It is possible to configure the interfacing region 120 to accept multiple sizes of introducer sheaths 24 without having steps. One solution is to gradually taper the interfacing region 120 to accommodate a range of different-sized introducer sheaths 24. Additionally both steps and tapers can be combined to accommodate a range of different introducer sheath diameters.

Figure 13:
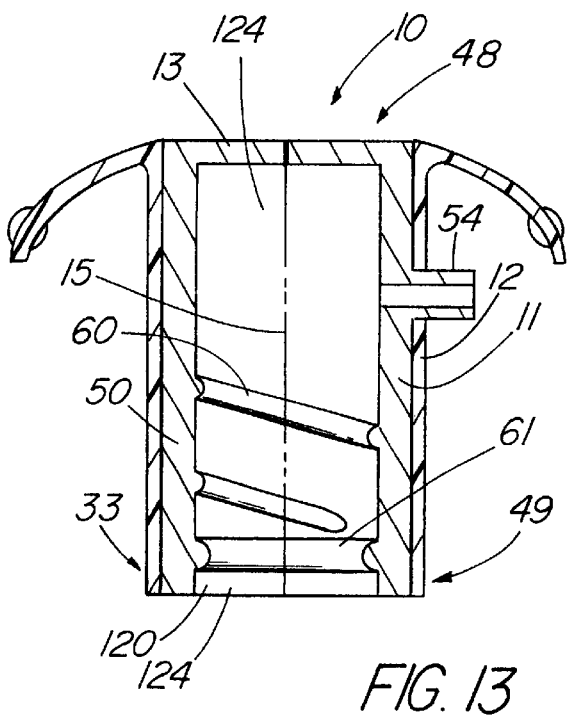
FIG. 13 depicts a cross-sectional view of an embodiment of the present invention adapted for placement over a proximal fitting.

Other types of introducer sheaths 24 and tubular medical conduits 23 for whose functionality could be improved by the present invention often include large proximal hubs or fittings, such as luer fittings, that the splittable valve assembly 10 must fit over in order to provide a proper seal. FIG. 13 depicts an embodiment in which the distal portion 33 of the hemostatic valve 11 includes a coupling mechanism 60 such as threads that allow the hemostatic valve assembly 10 to be placed over an introducer sheath with a fitting such as a luer lock hub. A valve O-ring 61, located within the passageway 14 toward the distal end 49, provides a seal 13 that is located against or below the fitting when the tubular medical conduit 23 is coupled to the hemostatic valve 11. It is also contemplated that the coupling mechanism 60 could be eliminated with the distal portion 33 being adapted to slide over and seal a standard proximal hub or fitting. This could occur by configuring the distal portion 33, which would include a series of seals 13 or O-rings 61, such that it can resiliently stretch over large fittings and provide a tight seal for a variety devices. Requirements include making the passageway of a sufficient diameter to accommodate the fitting, constructing the valve body 50 from a sufficiently elastic material to provide adequate contact with the fitting, and appropriately configuring the seal 13 or seals that would lie distal to the fitting to prevent flashback of blood after the hemostatic valve assembly 10 is in place.

Figure 34:
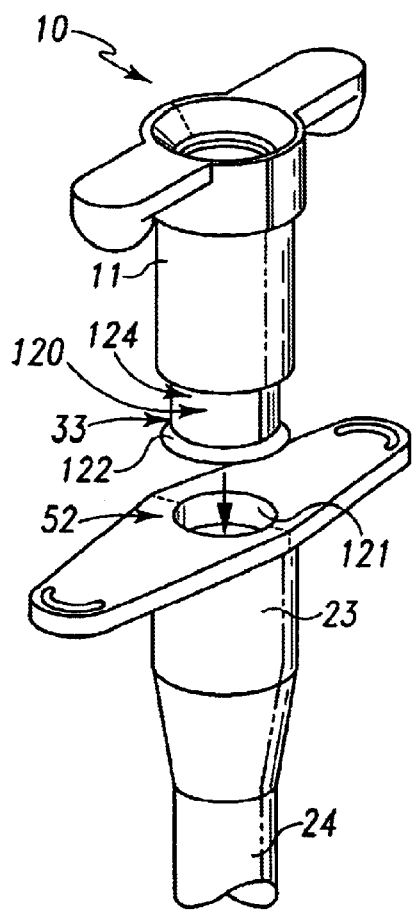
FIG. 34 depicts an embodiment of the present invention adapted to be placed within the passageway of an introducer sheath.

FIG. 34 depicts an second main type of interfacing region 120 in which the contact surface 124 with the tubular medical conduit 23 occurs on the outside surface of the hemostatic valve 11 such that at that the distal end 49 is inserted into the passageway 121 of the tubular medical conduit 23. In the illustrative embodiment, the passageway 121 represents a proximal receiving chamber that has been specially configured to mate with the distal portion 33 of an appropriately configured hemostatic valve 11. An optional distal lip 122 is included at the distal end 49 of the hemostatic valve 11 to help couple the valve within the passageway 122. Additionally or alternatively, the proximal end 52 of the tubular medical conduit 23 could be modified to include a locking lip similar in structure to element 111 of the hemostatic valve 11 depicted in FIGS. 31–33. The interfacing region 120 of the embodiment of FIG. 34 is configured such that only the distal portion of the valve body 50 is inserted into the proximal receiving chamber 122 of the introducer sheath 24; however it is also within the scope of the invention to have all or a substantial portion of the hemostatic valve be inserted into the passageway 121 of the introducer sheath 24 as depicted in FIGS. 14–18.

Included in the embodiments of FIGS. 9,13, and 31–33 is a side port 54 that communicates with the central passageway 14. The side port 54 can be used for a variety of purposes, for example, slow-drip intravenous administration (e.g., 1–10 cc/hr) to keep the vein open and prevent coagulation. A length of tubing 123, as depicted in FIG. 33, is attached to the side port 54 which in turn, would include a luer lock port or similar-type fitting to connect with the I.V. line at the end distal to the patient. The side port 54 would be available to perform other functions such as infusion of medicaments, saline for flushing, or contrast media. It would also have utility for instances when air must be evacuated from the system. The side port 54 of FIG. 33 is depicted as a nipple over which the tubing 123 is attached; however, other embodiments are possible such as a luer or other fitting, or merely an aperture into which the tubing 123 is inserted.

In various embodiments depicted in FIGS. 1–2, 4–5, and 12–13, the hemostatic valve assembly 10 of the illustrative embodiment further comprises a section of outer sheath 12 material that surrounds the hemostatic valve 11 and offers structural reinforcement and an alternative means of splitting the hemostatic valve 11 open to expose the passageway 14. In the illustrative embodiment of FIG. 1, the outer sheath 12 comprises a thin-walled tube of an molecularly-oriented, anisotropic material such as polytetrafluoroethylene (PTFE) whose molecular properties permit it to be torn longitudinally along a predetermined split line 16 whose path is determined by a cut point 55 formed in the material. The cut point 55 comprises a V-shaped notch in the illustrative embodiment, although a short linear cut could also work. The cut point 55 provides a starting point for the tear such that when the grasping members 40 are pulled apart, the tear continues from cut point 55 and maintains a straight path along the predetermined split line 16 that extends from cut point 55, thereby separating the outer sheath 12 longitudinally into two pieces. Separation of the outer sheath 12 permits the hemostatic valve 11 to also separate, which allows the hemostatic valve assembly 10, when no longer needed during the procedure, to be removed from an indwelling medical device without having to slide the valve over the proximal end of the indwelling device, which may be precluded if the device has a proximal fitting larger than the passageway 14 of the hemostatic valve 11. In the embodiment of FIG. 5, the hemostatic valve 11 has been pre-split into two halves 20,21 and then glued together with a layer of adhesive 41 such as silicone adhesive. Because the outer sheath 12 constrains the hemostatic valve 11, it should be noted that the hemostatic valve 11 can be split into two mated valve halves 20,21 that are not interconnected, but rather only held together by the inward radial force of the outer sheath 12. For example, by taking a split 7.0 Fr O.D. hemostatic valve 11 and pressure fitting the two valve halves 20,21 together inside a 7.0 Fr I.D. outer sheath 12, the resiliency and surface properties of the silicone material help provide a good seal along the lines of fissure 15. When the sheath is removed, the first and second valve halves 20,21 fall away from each other. Although a material having preferred directional properties such as anisotropic PTFE is preferred, the present invention encompassed any known method of predisposing a sheath to separate along a predetermined split line. Other methods of making a sheath splittable include scoring or perforating the walls of the sheath. Also included are multi-layered sheaths where one or more split or scores sheath layers are bonded to regular sheath to guide the tear through the underlying solid sheath, or subjecting the outer sheath 12 material to chemical or energy treatment along a desired predetermined split line 16 to create a preweakened feature.

In reference to FIG. 1, the integral tabs 46 not only serve as grasping members 40 for the clinician to separate the hemostatic valve 11, they also provide a means to secure the outer sheath 12 to the hemostatic valve 11 such that separation of the former results in the separation of the latter. Two longitudinally aligned apertures 38 are made through opposite sides of the outer sheath. A generally cylindrical die is used having recesses external to the apertures 38 such that when the silicone is injected into the die, it flows out the apertures 38 and cures to form a silicone bead 39 on the exterior surface 35 of the outer sheath 12. In the illustrative embodiment, the respective silicone beads 39 are molded so that they extend upward to the proximal end 48 of the hemostatic valve were they are extended outward to conveniently form the grasping members 40. In the embodiment of FIG. 2, the silicone bead 39 itself is not a grasping member 40, this function being provided by the ears 37 or extensions of the splittable PTFE material, and the associated handles 32 attached to the terminal ends of the ears 37. The embodiment of FIG. 2, shown also in cross-section in FIG. 4, basically represents a modified PEEL-AWAY® Introducer Sheath that has been truncated and coupled to an internal hemostatic valve 11. The outer sheath 12 forms a double layer 36 of material with the cut line 55 made to tear upward to the proximal end 48 of the assembly 10, then downward, continuing along the predetermined split line 16. The method of attaching the outer sheath 12 to the hemostatic valve 11 is not considered critical and as previously noted, an attachment is may not be necessary. In addition to the attachment method shown in FIGS. 1–2, the valve halves 20,21 can be bonded to the sheath with adhesive or another well-known method. When using PTFE, etching of the inner surface 17 can improve adherence of the hemostatic valve 11 to the outer sheath 12.

The hemostatic valve assembly 10 of the present invention, as shown in FIGS. 1–13 and 19–34, is used as a device that is separate from the splittable introducer sheath 24, or the hemostatic valve assembly 10 can be constructed such that the outer sheath 12 includes an introducer extension 18 as depicted in FIGS. 14–18, thereby obviating the need for a separate introducer. Essentially, the hemostatic valves 11 of these same embodiments, if not pre-coupled to the outer sheath 12 and distal extension 18, can also be regarded as a separate components from the sheath, such as the FIGS. 1–13 and 19–34 embodiments which are adapted to be placed into a separate tubular medical conduit 23 or introducer sheath 24. In either case, the interfacing region 120 extends a substantial portion (FIG. 16) or the entire length (FIGS. 15,17–18) of the external surface 35 of the valve. If the hemostatic valve 11 is not fixedly positioned within the introducer sheath 24/introducer extension 18 prior to use, this would allow the physician to insert the hemostatic valve into the introducer sheath 24 at some point into the procedure, and in some instances, back into the introducer sheath 24 once it has been partially peeled back to form a new proximal end. In the embodiment of FIG. 14, the outer sheath 12 and introducer extension 18 comprise a single tear-apart PTFE sheath that resembles the COOK PEEL-AWAY® Introducer Sheath with a hemostatic valve insert molded thereinside. Optionally, the hemostatic valve 11 may be attached to the outer sheath 12 in a manner similar to the embodiment of FIG. 2. The predetermined split line 16 extends the length of the outer sheath 12 and continues down the length of the contiguous introducer extension 18 as well. In another embodiment, the outer sheath configuration of FIG. 1, lacking the double layer 36 of material and ears 37 at the proximal end 48, can be simply modified to include a introducer extension 18 as well.

The embodiment of FIG. 15 depicts a simplified hemostatic valve 11 in which the seal 13 and valve body 50, are essentially united into a single cylindrical-shaped structure that is inserted into the outer sheath 12 and introducer extension 18 (or introducer sheath 24). In the illustrative embodiment, a single line of fissure 15 permits the intravascular medical device, such as a pacemaker lead, to be removed from the valve. Rather than being torn apart or falling apart from the splitting action of the outer sheath 12, the hemostatic valve 11 is simply slid off the lead via the line of fissure 15 when the two pieces 25,26 of the outer sheath 12/introducer extension 18 are torn away. More than one hemostatic valve 11 may be placed in the outer sheath 12 to be used in this manner. To prevent distal migration of the hemostatic valve 11 in embodiments where the hemostatic valve 11 and, the outer sheath 12 are not securely interconnected, the outer sheath 12 portion of the hemostatic valve assembly 10 can be made to have a slightly greater I.D. than that of the outer sheath/introducer extension 18 or introducer sheath 24.

Figure 17:
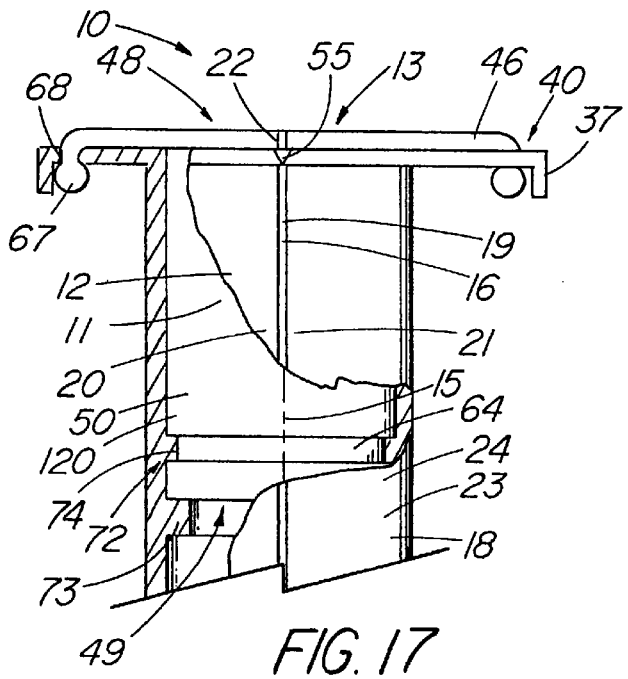
FIG. 17 depicts a partially-sectioned side view of a second embodiment that is adapted to be partially placed within an introducer sheath.

FIGS. 16–17 depict alternative embodiments having a number of features, including alternative methods of providing an secure interface between the hemostatic valve 11 and outer sheath 12. In the embodiment of FIG. 16, a band 63, which can be made of metal or hard plastic, is inserted into an annular recess 64 in the outer surface 35 of the valve body 50. The band 63 includes a series of teeth 65 that engage the inside surface 71 of the wall, preventing slippage of the hemostatic valve 11 toward the proximal end. Integral tabs 46 at the proximal end of the hemostatic valve 11 prevent its migration distally. Alternatively, the teeth 65 can be directed both proximally and distally to eliminate the need for making the proximal end of the hemostatic valve 11 larger than the outer sheath 12/introducer sheath 24. Having reverse-directed teeth 65 allows the physician to advance the hemostatic valve 11 into the sheath after it has been introduced into the patient, such as after a dilator has been removed. The band 63 can act as a means to hold the valve halves 20,21 together. In the illustrative embodiment the band 63 includes a break line 66 designed to fracture when the outer sheath 12 is separated. With the band 63 securing the two valve halves 20,21, can remain as separate pieces and the line of fissure 15 need not be aligned with the break line 66 or the predetermined split line 16 of the outer sheath 12. The teeth 65 embedded in the valve wall 47 provide a positive fixation that allows the band to separate along the break line 66. Alternatively, the band 63 can be made on only partially circumscribe the valve body 50 with the closed end being attached to the valve wall 47 of one valve half and not the other. Therefore, the C-shaped band 63 is pulled off the valve with the attached valve half, making a break line 66 unnecessary.

The embodiment of FIG. 17 depicts a hemostatic valve 11 with a annular recess 64, wherein the annular recess is used to receive projections 72, such as annular ridges, that are molded into the inner surface 17 of the other sheath 12 or introducer sheath 24. A second projection 73 distal to the position of the hemostatic valve 11 acts as a stop, while the proximal projection 74 prevents backward migration of the valve. The predetermined split line 16 of the outer sheath 12 or introducer sheath 24 in FIG. 17 comprises a preweakened feature 19 extending downward to the distal end of the sheath. The preweakened feature 19 can include a groove molded into the wall 47 of the outer sheath 12/introducer extension 18/introducer sheath 24 or the wall 47 can be scored after extrusion. In another aspect of the embodiment of FIG. 17, the hemostatic valve assembly 10 includes both integral tabs 46 on the hemostatic valve 11 and ears 37 extending laterally from the outer sheath 12/introducer sheath 24. The integral tabs 46 and ears 37 can be made to interlock as shown so that both form the grasping member 40, thereby creating additional force to separate the hemostatic valve assembly 10. In this particularly embodiment, the integral tabs 46 contain terminal knobs 67 that snap into receptacles 68 in the outer sheath ears 37.

Figure 18:
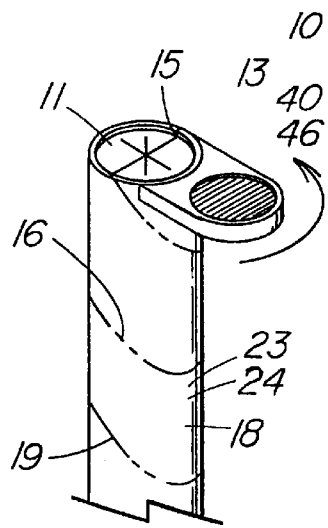
FIG. 18 depicts a pictorial view of an embodiment of the present invention used with a helical splitting introducer sheath.

In another embodiment shown in FIG. 18, the predetermined split line 16 of the outer sheath 12 and introducer extension 18 or introducer sheath comprises a helical-shaped preweakened feature 19, such as a groove, extending generally longitudinal along the length of the sheath. A single grasping member 40 is used to tear apart the outer sheath 12/introducer extension 18, resulting in a single piece of sheath material. The hemostatic valve 11 can be made to fall apart when the outer sheath 12 or introducer sheath is separated, or it may be attached to the outer sheath near a line of fissure such that when splitting of the sheath is initiated, the valve body 50 is at least partially slit along a line of fissure 15.

Figure 21:
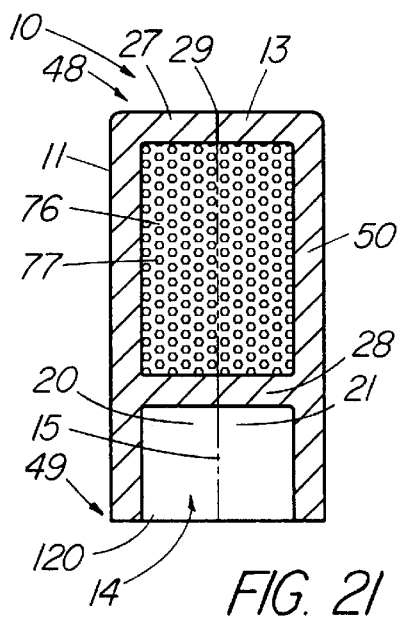
FIGS. 21–22 depict cross-sectional views of a hemostatic valve having a sealant filler material therein.

To improve sealing performance, which is especially desirable for arterial applications, FIG. 21 depicts a hemostatic valve embodiment that provides an increase in protection against blood flashback. Lying between the proximal seal 27 and the distal seal 28 is a valvular cavity 76 in which a sealant filler material 77 is placed to provide an additional blood barrier. This sealant filler material 77 can comprises virtually any biocompatible material capable of filling the valvular cavity and allowing passage of an intravascular device therethrough. Possible materials include, but are not limited to, a viscous liquid, such as glycerine; a gel; a foam (such as silicone); a sponge material; densely-packed solid particles such as minute beads or fibrous material; and strips of material such as collagen. Collagen and other certain other materials are able to absorb and retain blood providing an additional mechanism of protection. A pathway may be preformed through the sponge or other solid material to ease the passage of a medical device. Materials can be used in combination, for example, a gel-impregnated foam or collagen sponge. Solid materials can be affixed to, or incorporated into the valve body 50 so that they are carried away with the respective valve halves 20,21 during separation. In embodiments such as FIG. 6 and FIG. 8 having more than one valvular cavity 76, each can be filled with material and these materials can vary between the valvular cavities 76. The sealant filler material 77 of the illustrative embodiment can be placed in the placed within the mold prior to fabrication, placed within the valvular cavity 76 after the valve has been presplit, or injected into the valve, including through a side port 54 as shown in FIG. 13 or 31–33 or through the valve wall 47 using a small or non-coring needle. If so desired, a fluidized sealant filler material 77 could be aspirated from the valvular cavity 76 via the side port 54 prior to splitting the hemostatic valve 11, at which time any contents of the cavity would be exposed and be subject to leakage.

Figure 22:
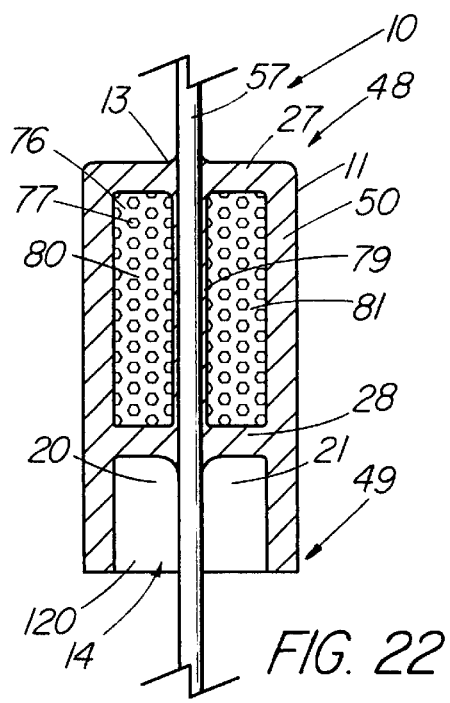
Figure 23:
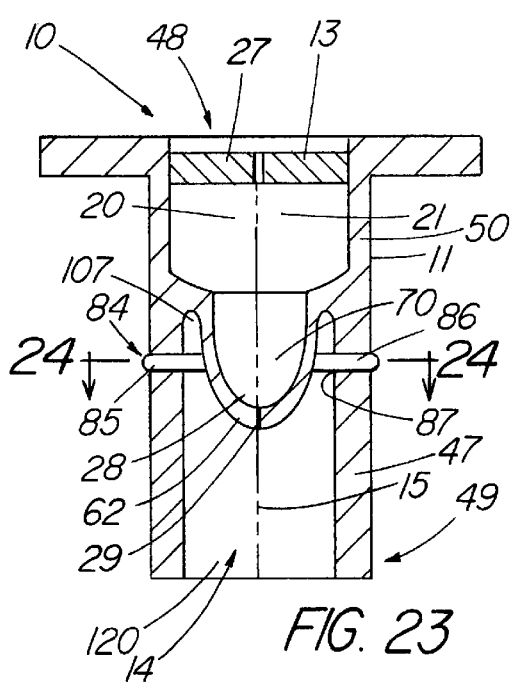
FIG. 23 depicts a cross-sectional view of a hemostatic valve having a biasing means.

As shown in FIG. 22, a liquid, foam, gel, or other semi-solid or resilient solid material can be contained within the valvular cavity 76 by the inclusion of one or more longitudinal membranes 79 that divide the valvular cavity 76 into two subcavities 80,81. In the illustrative embodiment, each subcavity is enclosed by a longitudinal membrane 79 and completely filled with a sealant filler material 77 such as gel or foam. When an intravascular device 57 such a dilator, pacemaker lead, etc., is introduced through the passageway 14 of the hemostatic valve 11, the filled subcavities 80,81 which have been laterally compressed by the introduced device, each exert a counteracting force upon the device and thus, provide a seal to impede blood flashback passing through the distal seal 28 at the distal end of the valvular cavity 76. During separation of the hemostatic valve 11, the valve halves fall away and the contents of the subcavities 80,81 remain intact.

Figure 25:
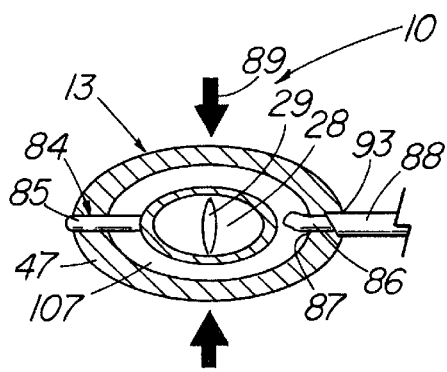
FIG. 25 depicts the embodiment of FIG. 24 during the manufacturing process.
Figure 24:
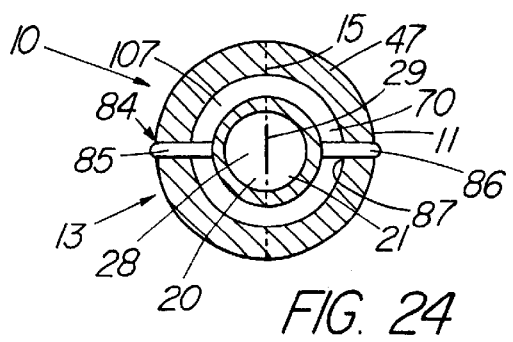
FIG. 24 depicts a cross-sectional view taken along line 24—24 of the embodiment in FIG. 23.

Referring now to FIGS. 23–28, the hemostatic valve assembly 10 of the present invention can also include a biasing means 84 that urges the valve leaflets together, thereby providing improved functionality to the sealing element 13, which in the illustrative embodiments, include the distal seal 28 comprising a duck-bill valve 70. In the embodiment depicted in FIGS. 23–25, the biasing means 84 comprises a first and a second biasing member 85,86 that are added to the valve assembly 10 after fabrication of the main hemostatic valve 11 body. In the illustrative example in which the body of the valve 11 is made of silicone, the first and second biasing members 85,86 comprise additional silicone material that is applied against each of the opposing valve leaflets 62 and allowed to cure. One example of manufacture is depicted in FIG. 25 wherein the steps include the application of external force 89 to the valve 11 using a fixture (not shown) capable of maintaining the valve in a given position. The force 89 is applied at opposite points along the circumference of the valve such that it is aligned with the main slit 29 that is to be urged closed. This causes the slit 29 to open slightly as the valve body 11 is deformed from its original circular cross-sectional shape. With the hemostatic valve 11 in a deformed condition, the material 92 that will form the second biasing member 86 (shown in FIG. 24) is applied, using an injection device 88 such as a syringe, within an intravalvular space 107 between the inner surface of the passageway 14 and a leaflet 62 of the distal valve 28. In the illustrative embodiment, the biasing material 92 is injected through an aperture 87 in the valve wall and allowed to cure while the pressure is maintained on the valve. The procedure is repeated for the opposing leaflet on opposite side of the valve 11. An alternative method of providing biasing material 92 that functions as a biasing means 84 is to inject the material 92 into the same intravalvular space 107 via the main passageway 14, rather than through an aperture 87 in the valve wall. Once curing has taken place, the external force 89 that is compressing the valve is removed, allowing the valve to return to its previous shape. As it does, each biasing member 85,86 urges the respective opposing leaflets 62 together. This cantilever action provided by the biasing members 85,86 allows the valve to maintain the desired level of function under higher backflow pressures than might be otherwise possible.

Another embodiment that includes a biasing means 84 is depicted in FIG. 26. The embodiment includes separate ring element 90 that is placed over the sealing element 13 (duckbill valve 70) to urge the leaflets 62 closed. The ring element 90, a top view of which is shown in FIG. 27, can be comprise a rubber O-ring or some other material, such as metal, and is placed within the central passageway 14 into the valvular space 107 to hold the leaflets 62 of the valve 11 together. In the illustrative embodiment, the ring element 90 has an ovoid configuration with lines of fissure 94 that align with the those of the valve body, as well as aligning with the main slit 29. The ring element 90, being elastic, is compressed into a more rounded configuration to permit the duck-bill valve 70 to pass therethrough, whereby the ring element 90 is released to impinge on the leaflets 62 of the sealing element 13 to urge them closed. As noted, the lines of fissure 94 permit the ring element 90 to be separated when the two halves 20,21 of FIG. 26 are split apart during removal of the valve assembly 10.

Figure 28:
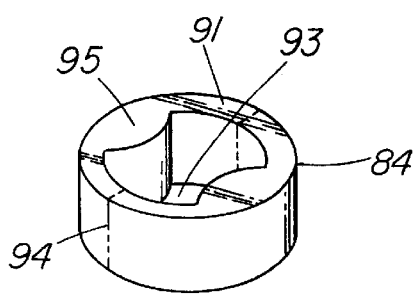
FIG. 28 depicts a pictorial view of a third embodiment of a biasing means.

FIG. 28 depicts yet another embodiment of a biasing means 84 comprising a sleeve 91 that functions in a manner similar to that of the ring element 90 of FIGS. 26–27. The sleeve 91 of the illustrative embodiment features an optional thickened portion 95 that projects into the aperture space 93 of the sleeve 91 and acts to further urge the valve closed when the latter is situated therewithin. The embodiments of FIGS. 26–27 are merely exemplary constraining elements and certainly do not represent the full range of possibilities that exist. Those skilled in medical arts would recognize that a multitude of configurations and materials are possible for constructing a suitable biasing means 84 that yields the desired characteristics. Although the illustrative embodiments each include lines of fissure 15 for splitting the valve 11 to expose the central passageway 14, conventional, non-splittable valves that include the disclosed biasing means 84 are to be considered to all within the scope of the invention.

Referring now to FIGS. 29–30, the valve assembly 10 of the present invention can include a plurality of valves 11 or proximal seals 28, each with separate passageways that merge into a central common passageway 100 that communicates with a common introducer sheath or medical conduit, therein allowing multiple devices to be used together without the disadvantage of having to share a common sealing element 13. For example, dual-chamber cardiac pacing requires introduction of separate leads for placement in both the atrium and the ventricle. The embodiment of FIGS. 29–29A, which includes a first proximal seal 27 and a second proximal seal 96, allows each lead to enter the introducer sheath over which the valve assembly 10 is situated via a dedicated sealing element 13, rather than requiring that a single sealing element 13 provide a tight seal for a pair of leads passing therethrough. Having dedicated proximal seals 27,96 for each device can also allow the clinician to better identify and track the individual leads or devices being placed during a procedure, especially if indicia 108 are used to distinguish the different proximal seals. These indicia 108 can include unique alphabetic or numeric identifiers, such as shown in the figure, or other standard means such as color coding, dots, different shapes, etc. The first and second proximal seals 27,96 communicate with a first and a second passageway 97,98, respectively, which unite distal to the point of bifurcation 99 to form a central common passageway 100 as depicted in FIG. 29A. In the illustrative embodiment, the main passageway 14 is designed to receive the proximal end of a standard or splittable introducer, however, the valve assembly 10 can include an integral introducer (introducer extension 18) such as in the embodiment of FIG. 14.

In reference to FIG. 29, the lines of fissure 15 are locate such that each of the proximal seals 27,96 are split down the middle along a main slit 29 when the two halves 20,21 of the valve assembly 10 are separated from each other by pulling apart the integral tabs 46. When the valve assembly includes a third proximal seal 104 such as in the embodiment depicted in FIG. 30, the valve assembly 10 is preferably configured to separate into three portions 101,102,103 with the lines of fissure 15 that divide the respective portions being configured to split two adjacent proximal seals 27,96, 104 along the centrally located slit 29 of each. All three of the lines of fissure 15 converge at a central point 109 located between the three proximal seals 27,96,104. As with the embodiment of FIGS. 29–29A, the three proximal seals 27,96,104 of FIG. 30 each communicate with dedicated passageways that join distally to form a central common passageway 100. One can appreciate that embodiments having more that three sealing elements 13 and passageways are possible, each proximal seal added generally requiring an additional line of fissure and corresponding portion in order that the valve assembly 10 can be split and removed from around each of the multiple devices that remains in position.

It is thus seen that the present invention has utility in a variety of medical procedures, and that variations and modifications of the splittable valve assembly of the present invention additional to the embodiments described herein are within the spirit of the invention and the scope of the claims.

What is claimed is:

1. A splittable valve assembly comprising:
   a hemostatic valve comprising a valve body and a passageway extending therethrough, the valve body including a wall having at least one line of fissure configured such that the hemostatic valve can be split at least partially open to expose the passageway, thereby allowing removal of a first medical device when situated therein; and
   a first sealing element traversing the passageway, the first sealing element configured to be self-sealing for preventing flow of bodily fluid therethrough; and
   a second sealing element traversing the passageway, the second sealing element comprising a foam material and having an aperture extending therethough, the aperture having an inside dimension selected to seal against said first medical device when situated therein.

2. The splittable valve assembly of claim 1 further including a valvular cavity, the valvular cavity at least partially filled will a sealant filler material.

3. The splittable valve assembly of claim 1 wherein said first sealing element comprises a plurality of proximal seals that include at least a first seal communicating with a first sub-passageway and a second proximal seal communicating with a second sub-passageway, the first and second sub-passageways uniting at a bifurcation point located within the passageway of the valve body.

4. The splittable valve assembly of claim 1 wherein the valve body comprises a substantially rigid polymeric material.

5. The splittable valve assembly of claim 1 wherein the first sealing element comprises a tulip-shaped valve having a plurality of valve leaflets, the splittable valve assembly further including at least one biasing mechanism positioned within the passageway so as to urge the plurality of valve leaflets into a closed position.

6. The splittable valve assembly of claim 5 wherein the biasing mechanism includes a first and a second biasing member oppositely placed within the passageway to urge the plurality of leaflets closed.

7. The splittable valve assembly of claim 5 wherein the biasing mechanism includes a annular ring located within the passageway such that it surrounds the tulip-shaped valve and urges the plurality of leaflets closed.

8. The splittable valve assembly of claim 1 wherein the hemostatic valve further comprises an interfacing region configured such that the splittable valve assembly can be detached and reattached to a second medical device.

9. The splittable valve assembly of claim 1, wherein the valve body further includes an interfacing region, the interfacing region configured such that the hemostatic valve is attachable to a separate second medical device, thereby at least substantially eliminating or preventing fluid loss therefrom.

10. The splittable valve assembly of claim 1, wherein the second sealing element comprises a disk of silicone foam that is inserted into and affixed within the passageway of the valve body.

11. The splittable valve assembly of claim 1, wherein the second sealing element includes a transverse fissure formed at least partially therethrough, thereby facilitating having the seal split along with the remainder of the hemostatic valve.

12. A splittable valve assembly comprising:
a hemostatic valve comprising a valve body and a passageway extending therethrough, the valve body including a wall having at least one line of fissure configured such that the hemostatic valve can be split at least partially open to expose the passageway, thereby allowing removal of a first medical device when situated therein; and
a first sealing element traversing the passageway, the first sealing element configured to be self-sealing for preventing flow of bodily fluid therethrough; and
a second sealing element traversing the passageway, the second sealing element comprising a disk of silicone foam material affixed to the valve body wall having a transverse fissure formed at least partially therethrough aligned with the at least one line of fissure in the valve body wall facilitating having the seal split along with the remainder of the hemostatic valve, the seal having an aperture extending therethrough, the aperture having an inside dimension selected to seal against said first medical device when situated therein.

13. The splittable valve assembly of claim 1 or 12 wherein the valve body comprises a non-rigid, elastomeric material.

14. The splittable valve assembly of claim 13 wherein at least one of the sealing elements is integral with the wall of the valve body.

15. The splittable valve assembly of claim 13 wherein there are two opposing lines of fissure that longitudinally define a first valve half and a second valve half.

16. The splittable valve assembly of claim 15 wherein the first half valve half and the second valve half each include an integral tab adapted for grasping and separating the first and second valve halves.

17. The splittable valve assembly of claim 13 further including a splittable introducer sheath having a first proximal end removably coupled to the hemostatic valve, wherein the hemostatic valve and splittable introducer sheath are each configured such that when the hemostatic valve is removed from the first proximal end of the splittable introducer to allow the splittable introducer sheath to partially split lengthwise thereof, thereby forming a new, second proximal end, the hemostatic valve can be placed over the second proximal end to at least substantially eliminate fluid loss therefrom.

18. The splittable valve assembly of claim 13 wherein the hemostatic valve further comprises an interfacing region configured for placement within the passageway of a splittable introducer sheath.

19. The splittable valve assembly of claim 13 wherein the non-rigid, elastomeric material includes silicone.

20. The splittable valve assembly of claim 13 further including an outer sheath made of a non-rigid material, the outer sheath having an inner surface and at least one predetermined split line, the outer sheath circumferentially enclosing at least a portion of the hemostatic valve.

21. The splittable valve assembly of claim 20 wherein the lines of fissure extend completely through the wall of the hemostatic valve such that first and second valve halves of the hemostatic valve are separate components being held together by radially constraining forces of the outer sheath.

22. The splittable valve assembly of claim 21 wherein the first valve half is affixed to the outer sheath at a first attachment point and the second valve half is attached to the outer sheath at a second attachment point, the first and second attachment points being separated by at least one of the predetermined split line such that any splitting of the outer sheath results in the first and second valve halves being forced apart, while each remaining affixed to the outer sheath.

23. The splittable valve assembly of claim 20, wherein the outer sheath provides an enclosure along a substantial portion of the hemostatic valve.

24. The splittable valve assembly of claim 23 wherein the outer sheath extends distally from the hemostatic valve to form an introducer extension, said at least one predetermined split line extending substantially entirely along the introducer sheath.

25. The splittable valve assembly of claim 24, wherein the outer sheath comprises a polymer having an isotropic properties to facilitate tearing the outer sheath along the at least one predetermined split line.

26. The splittable valve assembly of claim 24, wherein the at least one predetermined split line comprises a preweakened feature.

27. The splittable valve assembly of claim 13 wherein the hemostatic valve further includes a proximal locking chamber configured to accept a proximal hub of a dilator to at least temporarily secure the hub therein, thereby preventing movement of the dilator relative to the hemostatic valve.

28. The splittable valve assembly of claim 13 wherein hemostatic valve further comprises an interfacing region including a plurality of steps, each of the plurality of steps sized for placement over a different-diameter tubular medical conduit.

29. A splittable valve assembly comprising:
a hemostatic valve comprising a valve body made of a silastic material and a passageway extending therethrough, the valve body including a wall having two opposing lines of fissure that longitudinally define a first valve half and a second valve half such that the hemostatic valve can be split open along the lines of fissure in order to remove the hemostatic valve from around an first medical device when situated therein, each valve half including a grasping element comprising an integral tab;

a proximal receiving chamber configured to accept a proximal hub of a dilator to at least temporarily secure the hub therein, thereby preventing movement of the dilator relative to the hemostatic valve; and a plurality of sealing elements traversing the passageway that include a distal seal that is integral with the valve body, and a proximal seal comprising a valve insert, the valve insert comprising a foam material and including an aperture therethough, the aperture having an inside dimension selected to seal against said first medical device when situated therein;

wherein the valve body further includes an interfacing region, the interfacing region configured such that the hemostatic valve may be placed over a proximal end of an introducer sheath, thereby substantially eliminating or preventing fluid loss therefrom, the interfacing region further comprising a plurality of steps, each of the plurality of steps sized for placement over a different-diameter splittable introducer sheath.

30. The splittable valve assembly comprising:

a hemostatic valve comprising a non-rigid, elastomeric material and which includes a valve body and a passageway extending therethrough, the valve body including a wall having at least one line of fissure configured such that the hemostatic valve can be split open to expose the passageway, thereby allowing removal of a first medical device when situated therein;

a first, proximal sealing element traversing the passageway, the first sealing element configured to be self-sealing for preventing flow of bodily fluid therethrough;

a second, distal sealing element traversing the passageway, the second sealing element comprising a foam material and having an aperture extending therethrough, the aperture having an inside dimension selected to seal against said first medical device when situated therein; and wherein the valve body further includes an interfacing region, the interfacing region configured such that the hemostatic valve is attachable to a separate second medical device, thereby at least substantially eliminating or preventing fluid loss therefrom.

* * * * *

UNITED STATES PATENT AND TRADEMARK OFFICE
CERTIFICATE OF CORRECTION

PATENT NO. : 6,712,791 B2 Page 1 of 1
DATED : March 30, 2004
INVENTOR(S) : Chun Kee Lui It is certified that error appears in the above-identified patent and that said Letters Patent is hereby corrected as shown below:

<u>Column 18,</u>
Line 46, change "an isotropic" to -- anisotropic --

Signed and Sealed this

Thirteenth Day of July, 2004

JON W. DUDAS
*Acting Director of the United States Patent and Trademark Office*